United States Patent [19]
Nakanishi et al.

[11] Patent Number: 5,847,181
[45] Date of Patent: Dec. 8, 1998

[54] PREPARATION OF ALKYLHALOSILANES

[75] Inventors: Tetsuo Nakanishi; Tetsuya Inukai, both of Gunma-ken; Kazumasa Tsukioka, Annaka; Hiroshi Nakayama, Annaka; Yukinori Satoh, Annaka, all of Japan

[73] Assignee: Shin-Etsu Chemical Co., Ltd., Tokyo, Japan

[21] Appl. No.: 812,942

[22] Filed: Mar. 4, 1997

[30] Foreign Application Priority Data

Dec. 13, 1996 [JP] Japan .................................. 8-353019

[51] Int. Cl.$^6$ ........................................................ C07F 7/16
[52] U.S. Cl. ................................................................ 556/472
[58] Field of Search .............................................. 556/472

[56] References Cited

U.S. PATENT DOCUMENTS

| | | | |
|---|---|---|---|
| 2,380,995 | 8/1945 | Rochow | 260/607 |
| 4,500,724 | 2/1985 | Ward, III et al. | 556/472 |
| 4,602,101 | 7/1986 | Halm et al. | 556/472 |
| 4,762,940 | 8/1988 | Halm et al. | 556/472 |
| 4,898,960 | 2/1990 | Dosaj et al. | 556/472 |
| 4,946,978 | 8/1990 | Halm et al. | 556/472 |
| 5,059,343 | 10/1991 | Halm et al. | 556/472 |
| 5,059,706 | 10/1991 | Degen et al. | 556/472 |
| 5,068,385 | 11/1991 | Degen et al. | 556/472 |

FOREIGN PATENT DOCUMENTS

| | | |
|---|---|---|
| 92421 | 8/1989 | Japan . |
| 122749 | 1/1959 | U.S.S.R. . |
| 178817 | 2/1966 | U.S.S.R. . |
| 237892 | 2/1969 | U.S.S.R. . |

*Primary Examiner*—Paul F. Shaver
*Attorney, Agent, or Firm*—Birch, Stewart, Kolasch & Birch, LLP

[57] ABSTRACT

An alkylhalosilane is prepared by charging a reactor with a contact mass comprising metallic silicon powder and a copper catalyst and feeding a reactant gas containing an alkyl halide into the reactor whereby the silane is formed by direct synthesis. A phosphorus compound is added to the contact mass in an amount of 3,000–10,000 ppm calculated as phosphorus. The invention produces a more amount of dialkyldihalosilane in a desirable STY while minimizing the amount of unnecessary disilanes.

12 Claims, No Drawings

PREPARATION OF ALKYLHALOSILANES

BACKGROUND OF THE INVENTION

1. Field of the Invention

This invention relates to an improvement in the direct process for preparing an alkylhalosilane and more particularly, to a process for continuously preparing an alkylhalosilane by gas-solid contact reaction between metallic silicon and alkyl halide in the presence of a copper catalyst.

2. Prior Art

With respect to the synthesis of alkylhalosilanes, Rochow first disclosed in U.S. Pat. No. 2,380,995 direct synthesis reaction between metallic silicon and an alkyl halide in the presence of a copper catalyst. Since then, there have been reported a number of research works relating to various co-catalysts used together with copper catalysts, various copper catalysts and treatment thereof, reactors, additives used during reaction, and the like.

The direct synthesis process involves activating a contact mass comprising metallic silicon and a copper catalyst and introducing an alkyl halide into the activated contact mass for accomplishing gas-solid direct contact between metallic silicon and alkyl halide, thereby producing alkylhalosilanes.

In the industrial synthesis of alkylhalosilanes, the selectivity and formation rate of dialkyldihalosilane are crucial because the dialkyldihalosilane is used most often in silicone products. The selectivity of dialkyldihalosilane is evaluated in terms of a weight or molar ratio of dialkyldihalosilane to the silanes produced and a T/D ratio. Alkylhalosilane products contain dialkyldihalosilane (D), trialkylhalosilane (M), alkyltrihalosilane (T), etc. as well as other by-products such as alkylhydrodihalosilane (H) and alkylhalodisilane. In particular, disilanes are known as a residue or waste among silane manufacturers because few methods are available for the effective utilization of disilanes and most disilanes are discarded. The T/D ratio is a compositional ratio of alkyltrihalosilane to dialkyldihalosilane in the entire alkylhalosilanes produced, with a lower T/D ratio being preferred. The formation rate of alkylhalosilanes is represented by a space time yield (STY) which is the weight of crude alkylhalosilanes produced per unit time relative to the weight of metallic silicon held in the reactor. In order to improve the content of dialkyldihalosilane produced, reduce the T/D ratio or increase the STY, various research works have been made with a focus on the catalyst and accelerator.

USSR Application Specification No. 617,569 (Certificate of inventorship No. 122,749) dated 24 Jan. 1959 discloses reaction in the presence of a metallic silicon-copper alloy with 20 to 40 ppm of antimony added. Allegedly, the dimethyldichlorosilane content is improved from 40% to 60%. U.S. Pat. No. 4,500,724 discloses use of a copper/zinc/tin catalyst containing 200 to 3,000 ppm of tin, thereby achieving an improvement of T/D to 0.037. Japanese Patent Publication (JP-B) No. 92421/1994 discloses reaction using copper arsenide having an arsenic concentration of at least 50 ppm. It is described in these patent references that reactivity, more specifically the rate of reaction of metallic silicon is improved by adding these tin, antimony and arsenic co-catalysts to a reaction contact mass comprising metallic silicon and copper.

USSR Application Specification No. 903,369 (Certificate of inventorship No. 178,817) dated 6, Feb. 1964 discloses that a co-catalyst selected from the group consisting of zinc, bismuth, phosphorus (200 ppm), arsenic, tin, and iron improves the dimethyldichlorosilane content to 72.1% from the value achieved by the above-referred Application Specification No. 617,569 (Certificate of inventorship No. 122, 749). Also USSR Application Specification No. 1,152,943 (Certificate of inventorship No. 237,892) dated 20 Nov. 1969 discloses to add a phosphorus-copper-silicon alloy to a contact mass so as to give 2,500 to 30,000 ppm of phosphorus, thereby improving the dimethyldichlorosilane content to 82.3%. However, this USSR patent uses a metallic silicon alloy containing an accelerator, which is not suitable for reaction on a commercial scale, and STY and the silane composition are not satisfactory. Moreover, U.S. Pat. No. 4,602,101 corresponding to JP-B 51596/1993 discloses that 25 to 2,500 ppm of a phosphorus compound capable of generating elemental phosphorus in the reactor is added to a contact mass. Although the results of reaction according to this US patent are improved over the last-mentioned USSR patent, there still remain many problems including hazard imposed by spontaneously igniting elemental phosphorus and increased cost of raw materials. Then this US patent is also unsuitable to apply to commercial scale reactors. There is no teaching from which results of reaction with phosphorus concentrations of more than 2,500 ppm are expectable.

SUMMARY OF THE INVENTION

Therefore, an object of the present invention is to provide a process for preparing alkylhalosilane by direct synthesis, the process being capable of increasing the amount of dialkyldihalosilane produced in a desired STY while minimizing the amount of unnecessary disilanes.

The present invention pertains to the preparation of an alkylhalosilane by the commercially advantageous direct process, especially a direct alkylhalosilane preparing process capable of increasing the amount of dialkyldihalosilane produced in a desired STY while minimizing the amount of unnecessary disilanes. We have found that by adding a phosphorus-containing compound to a contact mass comprising metallic silicon in an effective amount, more specifically in an amount of 3,000 to 10,000 ppm calculated as the weight of phosphorus, formation of disilanes can be controlled while maintaining reactivity. Then the amount of dialkyldihalosilane produced can be increased. The present invention is predicated on this finding.

According to the invention, there is provided a process for preparing an alkylhalosilane of the general formula:

$$R_n SiX_{4-n}$$

wherein R is an alkyl group having 1 to 4 carbon atoms, X is a halogen atom, and letter n is an integer of 0 to 4 (i.e., 0, 1, 2, 3 or 4), comprising the steps of charging a reactor with a contact mass comprising metallic silicon powder and a copper catalyst, said contact mass containing a phosphorus compound in an amount of 3,000 to 10,000 ppm calculated as phosphorus, and feeding a reactant gas containing an alkyl halide into the reactor whereby the silane is formed by direct synthesis.

DETAILED DESCRIPTION OF THE INVENTION

Briefly stated, the process of the present invention is to prepare an alkylhalosilane through direct synthesis from metallic silicon powder and an alkyl halide in the presence of a copper catalyst.

The metallic silicon used herein should preferably have a purity of at least 97% by weight, especially at least 98% by weight. Preferred is metallic silicon powder obtained by crushing metallic silicon to an appropriate particle size. Where the reactor used is a fluidized bed reactor or agitation reactor, metallic silicon powder having a particle size of 5 to 150 μm is preferred in order that the metallic silicon powder have a good fluidization in the reactor. Note that the term "particle size" used herein is a particle size corresponding to 50% of a mass base cumulative oversize distribution curve by sieve analysis.

For the copper catalyst, any form of copper may be used, for example, elemental copper such as copper powder and stamped copper and copper compounds such as cuprous oxide, cupric oxide, and copper halides. An accelerator such as zinc, tin, antimony, and arsenic may be used as a co-catalyst. These accelerators may be used separately or as an alloy with copper. Exemplary accelerators are metallic zinc, tin, antimony, and arsenic powders, chlorides and oxides of zinc, tin, antimony, and arsenic, and copper alloys such as Cu—Zn, Cu—Sn, and Cu—Zn—Sn (or Sb or As). The copper catalyst may be loaded in the reactor alone or as an alloy together with metallic silicon powder. The loading of the copper catalyst is preferably about 0.1 to 10 parts, especially about 2 to 8 parts by weight of copper per 100 parts by weight of the metallic silicon powder. When the co-catalyst is used, the loading of zinc is preferably 0.05 to 1 part by weight per 100 parts by weight of the metallic silicon powder, and the loading of tin, antimony and arsenic alone or in admixture is preferably 0.001 to 0.05 part, especially 0.005 to 0.01 part by weight per 100 parts by weight of the metallic silicon powder.

According to the invention, a phosphorus compound is blended in the contact mass. Examples of the phosphorus compound which can be used herein include (i) metal phosphides such as phosphides of transition metals including W, Fe, Co, Ni, Cr, Mn, Cu, Bi, Mo, and Ti and (ii) metal phosphates such as tricalcium phosphate, calcium metaphosphate, and calcium pyrophosphate in anhydrous salt form and salts thereof with 1A and 2A Group metals such as sodium, potassium and magnesium and 1B and 2B Group metals such as copper and zinc.

Among these phosphorus compounds, phosphates are preferred from the standpoint of cost, with calcium pyrophosphate being most preferred. Since the metal phosphate generally contains a trace amount of water, it is preferred that the metal phosphate is previously heat treated at 200° C. or higher in order to remove water before the metal phosphate participates in reaction. The metal phosphates mentioned above are very stable compounds having a high melting point. Surprisingly, the metal phosphates maintain a steady effect over a long period of time without being decomposed into elemental phosphorus as disclosed in U.S. Pat. No. 4,602,101.

Where metal phosphides are used, it is preferred to select a metal phosphide free of the risk of impurity accumulation. However, even copper phosphide cannot avoid an unnecessary rise of copper concentration. Then the metal phosphides should preferably be used in a less amount than the metal phosphates.

The loading of the phosphorus compound (calculated as the weight of phosphorus) should be 3,000 to 10,000 parts by weight of phosphorus per million parts by weight of the contact mass comprising metallic silicon and catalyst. With less than 3,000 ppm of phosphorus added, the suppression of high-boiling compounds intended in the present invention is insufficient. More than 10,000 ppm of phosphorus can adversely affect reactivity. The preferred loading of the phosphorus compound is 4,000 to 8,000 ppm calculated as the weight of phosphorus.

Alkyl halides are reacted with metallic silicon to form alkylhalosilanes. Exemplary alkyl halides include methyl chloride, ethyl chloride, propyl chloride, methyl bromide, and ethyl bromide. Among these, methyl chloride is commercially most useful. Dimethyldichlorosilane prepared using methyl chloride finds numerous applications as a raw material for a variety of silicone products. Desirably the alkyl halide reactant is previously heated and gasified before it is fed into the reactor. The alkyl halide gas may be used alone or in admixture with an inert gas. The feed amount of alkyl halide gas is calculated as an amount (combined with the inert gas) necessary to fluidize the contact mass and hence, properly determined from the diameter of a reactor used and a superficial velocity in a column.

In the step of heating the contact mass or imparting catalytic activity to the contact mass, an inert gas is used for fluidizing the contact mass in the reactor. The inert gas used herein includes argon and nitrogen, with the nitrogen being preferred for economy. The flow velocity of inert gas may be at least the velocity at which the contact mass starts fluidizing, especially about 5 times the fluidization starting velocity. If the flow velocity of inert gas is below this range, uniform fluidization of the contact mass would be difficult. If the flow velocity of inert gas is beyond this range, more metallic silicon powder would scatter and the loss of inert gas and heat would increase. It is preferred to flow the inert gas in a circulating manner.

After the contact mass is given catalytic activity as mentioned above, the alkyl halide is introduced into the reactor whereby gas-solid contact reaction takes place between the alkyl halide and metallic silicon to form an alkylhalosilane. The conditions of this gas-solid contact reaction may be the same as in conventional processes.

EXAMPLE

Examples of the present invention are given below by way of illustration and not by way of limitation. All parts are by weight.

Examples 1–4 and Comparative Example 1

A fluidized bed reactor of carbon steel having a diameter of 50 mm and a height of 300 mm was charged with 100 parts of metallic silicon powder and 4 parts of a catalyst mixture comprising metallic copper powder. The phosphorus compound shown in Table 1 was also loaded in a varying amount.

Thereafter, methyl chloride was admitted into the reactor at a flow velocity of 1.3 cm/sec. and the temperature within the reactor was increased to 330° C. for reaction to continue. Reaction was terminated after 6 hours. Table1 shows the accumulative T/D and STY from the start to the end of reaction. Note that T/D is the weight (g) of methyltrichlorosilane divided by the weight (g) of dimethyldichlorosilane, both contained in the methylchlorosilanes produced. STY representative of a rate of formation of alkylhalosilane is equal to [the weight (g) of alkylhalosilanes]/[the weight (Kg) of metallic silicon×hour (hr)]. Table 1 also reports the proportion of dimethyldichlorosilane (D) and the proportion of high-boiling products (R) relative to the entire amount of methylchlorosilanes produced. Note that the high-boiling products are those products having a boiling point of higher than 70° C. under atmospheric pressure, such as disilanes in the methylchlorosilanes produced.

TABLE 1

|  | E1 | E2 | E3 | E4 | CE1 |
|---|---|---|---|---|---|
| Phosphorus compound | copper phosphide | calcium pyrophosphate | calcium metaphosphate | calcium pyrophosphate | none |
| P (ppm/mass) | 4,000 | 4,000 | 5,200 | 8,000 | 40 |
| STY (g/kg · hr) | 126 | 124 | 117 | 111 | 125 |
| D (wt %) | 90.8 | 90.5 | 89.9 | 90.3 | 88.4 |
| R (wt %) | 1.8 | 2.2 | 2.3 | 2.2 | 3.4 |
| T/D | 0.048 | 0.043 | 0.043 | 0.044 | 0.051 |

Example 5 and Comparative Example 2

Reaction was carried out on a pilot scale using a fluidized bed reactor of carbon steel having a diameter of 330 mm and a height of 8,000 mm. The reactor was charged with 100 parts of metallic silicon powder and 4 parts of a catalyst mixture comprising metallic copper powder. The phosphorus compound shown in Table 2 was also loaded in a varying amount.

Thereafter, methyl chloride was admitted into the reactor at a flow velocity of 18 cm/sec. and the temperature within the reactor was increased to 290° C. for reaction to continue. Reaction was terminated after 7 days. Table 2 shows the accumulative T/D and STY from the start to the end of reaction. Table 2 also reports the proportion of dimethyldichlorosilane (D) and the proportion of high-boiling products (R) relative to the entire amount of methylchlorosilanes produced. Note that the high-boiling products are those products having a boiling point of higher than 70° C. under atmospheric pressure, such as disilanes in the methylchlorosilanes produced.

TABLE 2

|  | E5 | CE2 |
|---|---|---|
| Phosphorus compound | calcium metaphosphate | none |
| P (ppm/mass) | 4,200 | 40 |
| STY (g/kg · hr) | 120 | 120 |
| D (wt %) | 89.5 | 88.4 |
| R (wt %) | 2.6 | 3.5 |
| T/D | 0.04 | 0.047 |

It is evident from the results that in the runs within the scope of the invention, the content of desired dialkyldihalosilane is higher and the content of high-boiling products is lower than in the runs without phosphorus addition. With respect to reactivity, the addition of 8,000 ppm of phosphorus compound invited a drop of only about 10% as compared with the runs without phosphorus addition. Thus the runs within the scope of the invention are advantageous.

By the inexpensive means of adding an effective amount of phosphorus compound to a conventional contact mass in a process for preparing alkylhalosilane by direct synthesis, the invention is successful in increasing the amount of dialkyldihalosilane produced in a desired STY while minimizing the amount of unnecessary disilanes. The productivity of a process for preparing alkylhalosilane by direct synthesis is significantly improved.

Although some preferred embodiments have been described, many modifications and variations may be made thereto in the light of the above teachings. It is therefore to be understood that within the scope of the appended claims, the invention may be practiced otherwise than as specifically described.

We claim:

1. A process for preparing an alkylhalosilane of the general formula:

$$R_n SiX_{4-n}$$

wherein R is an alkyl group having 1 to 4 carbon atoms, X is a halogen atom, and letter n is an integer of 0 to 4, comprising the steps of charging a reactor with a contact mass comprising metallic silicon powder and a copper catalyst, said contact mass containing a phosphorus compound in an amount of 3,000 to 10,000 ppm calculated as phosphorus, and feeding a reactant gas containing an alkyl halide into the reactor whereby the silane is formed by direct synthesis.

2. The process of claim 1 wherein the phosphorus compound is a metal phosphide or metal phosphate.

3. The process of claim 2 wherein the phosphorus compound is copper phosphide.

4. The process of claim 2 wherein the phosphorus compound is calcium phosphate.

5. The process of claim 1, wherein the reactor is a fluidized bed reactor or an agitation reactor.

6. The process of claim 1, wherein the metallic silicon powder has a particle size of 5 to 150 µm.

7. The process of claim 1, wherein the copper catalyst is present in an amount of about 0.1 to 10 parts by weight based on parts by weight of the metallic silicon powder.

8. The process of claim 7, wherein the copper catalyst is present in an amount of about 2 to 8 parts by weight based on 100 parts by weight of the metallic silicon powder.

9. The process of claim 1, wherein said phosphorus compound is present in an amount of 4,000 to 8,000 ppm calculated as phosphorus.

10. The process of claim 1, wherein said alkyl halide is selected from the group consisting of methyl chloride, ethyl chloride, propyl chloride, methyl bromide and ethyl bromide.

11. The process of claim 10, wherein said alkyl halide is methyl chloride.

12. The process of claim 1, wherein said alkyl halide is heated and gasified before it is fed into the reactor.

* * * * *